(12) United States Patent
Schoeniger et al.

(10) Patent No.: US 7,022,287 B2
(45) Date of Patent: Apr. 4, 2006

(54) SINGLE PARTICLE ELECTROCHEMICAL SENSORS AND METHODS OF UTILIZATION

(75) Inventors: Joseph Schoeniger, Oakland, CA (US); Albert W. Flounders, Berkeley, CA (US); Robert C. Hughes, Albuquerque, NM (US); Antonio J. Ricco, Los Gatos, CA (US); Karl Wally, Lafayette, CA (US); Stanley H. Kravitz, Placitas, NM (US); Richard P. Janek, Oakland, CA (US)

(73) Assignee: Sandia National Laboratories, Livermore, CA (US)

( * ) Notice: Subject to any disclaimer, the term of this patent is extended or adjusted under 35 U.S.C. 154(b) by 671 days.

(21) Appl. No.: 10/141,806

(22) Filed: May 8, 2002

(65) Prior Publication Data

US 2003/0211637 A1 Nov. 13, 2003

(51) Int. Cl.
*G01N 15/06* (2006.01)

(52) U.S. Cl. .................... 422/82.01; 422/68.1; 422/50; 257/236; 204/290.01; 204/290.03; 204/290.05

(58) Field of Classification Search .................. 422/50, 422/61, 68.1, 82.01, 82.02, 82.03; 435/7.1, 435/4, 7.93, 174, 283.1, 285.2, 287.1; 436/501, 436/806; 257/37, 27, 236, 24; 204/290.01–15
See application file for complete search history.

(56) References Cited

U.S. PATENT DOCUMENTS

| | | | | |
|---|---|---|---|---|
| 5,181,526 A | * | 1/1993 | Yamasaki | 607/121 |
| 5,393,401 A | * | 2/1995 | Knoll | 204/403.06 |
| 5,891,630 A | * | 4/1999 | Eggers et al. | 435/6 |
| 6,258,652 B1 | * | 7/2001 | Stacey | 438/238 |
| 6,358,819 B1 | * | 3/2002 | Shelton et al. | 438/433 |
| 6,566,276 B1 | * | 5/2003 | Maloney et al. | 438/758 |
| 6,653,653 B1 | * | 11/2003 | Brousseau, III | 257/39 |
| 6,673,717 B1 | * | 1/2004 | Brousseau, III | 438/674 |
| 2004/0005243 A1 | * | 1/2004 | Mulhern et al. | 422/58 |

* cited by examiner

Primary Examiner—Long V. Le
Assistant Examiner—Melanie Yu
(74) Attorney, Agent, or Firm—Timothy P. Evans

(57) ABSTRACT

The present invention discloses an electrochemical device for detecting single particles, and methods for using such a device to achieve high sensitivity for detecting particles such as bacteria, viruses, aggregates, immuno-complexes, molecules, or ionic species. The device provides for affinity-based electrochemical detection of particles with single-particle sensitivity. The disclosed device and methods are based on microelectrodes with surface-attached, affinity ligands (e.g., antibodies, combinatorial peptides, glycolipids) that bind selectively to some target particle species. The electrodes electrolyze chemical species present in the particle-containing solution, and particle interaction with a sensor element modulates its electrolytic activity. The devices may be used individually, employed as sensors, used in arrays for a single specific type of particle or for a range of particle types, or configured into arrays of sensors having both these attributes.

9 Claims, 6 Drawing Sheets

SINGLE PARTICLE ELECTROCHEMICAL SENSORS AND METHODS OF UTILIZATION

The United States Government has rights in this invention pursuant to Contract No. DE-AC04-94AL85000 between the United States Department of Energy and the Sandia Corporation for the operation of the Sandia National Laboratories.

BACKGROUND OF THE INVENTION

The present invention relates to particle detection devices, particularly to devices for single-particle detection and to methods for using the devices to achieve extremely high sensitivity detection of specific particles, and more particularly to devices for affinity-based electrochemical detection of particles with single-particle sensitivity, and wherein a single device or an array of devices employing surface-attached specific affinity components may be used to selectively capture particles.

Various approaches to detection of particles in a solution have been developed over the years. Molecular Recognition Materials (MRMs) capable of selective binding to a particle are used in a wide range of assays and sensors. Such materials include Antibodies (Abs) and natural receptor ligands for various biological particles, but may also include a range of synthetic MRMs including combinatorial peptides and other combinatorially produced materials and designed ligands and chelators. Abs may be considered the archetypal of MRMs, and are used in an enormous range of assays and sensors. Assays using MRMs may be divided according to whether they are homogenous (all reagents are mixed into a single phase and the result is read) or heterogeneous. In this second category, MRMs are generally immobilized onto a surface and then exposed to a solution containing particles, as described above. Commonly used formats include the ELISA assay and formats such as latex bead agglutination assays, but an enormous variety of implementations exists. These methods may be used for the range of particle types defined here (bacteria through molecules), but generally require a large number of the particles to be present. This is because affinity-based methods such as ELISA assays generally work on a continuum basis, rather than a statistical (i.e., single particle) basis.

For the detection and identification of bacteria or bacterial spores, viruses, or other pathogens, classical microbiological methods (in vitro and in vivo culture on selective media, colony morphology, chemical staining) still predominate. In the past two decades, the use of MRMs in the form of immunohistochemistry, coupled with light (i.e., fluorescence) or electron microscopy, has created alternative means of pathogen identification. Such methods may be adapted for automated identification of organisms through means such as fluorescence-based flow cytometry. More recently, Polymerase Chain-Reaction (PCR) methods have been developed that allow determination of whether a particular organism is present or not. PCR requires isolation of nucleic acids from the sample, and many cycles of reaction, typically taking on the order of 30 minutes or longer.

Both culture and PCR have the advantage that, in principle, even a single organism in a sample may be detached, although the amplification of material (through growth of organisms, or repeated reactions) that allows this required time. Formats such as flow cytometry, where each particle might be labeled with a selectively-binding fluorescent Abs, do permit rapid single particle detection, albeit generally in a rather large package. The problem is that the method has no way of confirming if a given single particle was actually the target analyte, or something to which the Abs bound through non-specific binding (NSB) interactions. To rule out NSB requires a secondary test, by means such as PCR or dissociating the Abs from the particle, re-labeling with a second MRM, and sending it through the flow cytometer system again while such systems are possible to implement, they compound the complexity, size, time, and reagent requirements of the original methods. There are also limitations in throughput for all of these methods, in that detecting a single particle in a given volume requires somehow processing at least that much volume (preferably several times the volume to allow for a given statistical level of surety). Again, although it is in principle possible to address these difficulties through scaling (multiple independent channels operating simultaneously), this can only be done at the cost of greater instrumental complexity.

Another concept that needs to be introduced is that it is advantageous if the process of measuring the presence of the particle does not destroy it. This then facilitates repeated measurements of the particle's properties, which can be used to confirm its presence and identity. For example, in flow cytometry, once the fluorescently-labeled particle passes through the laser-based fluorescence detection portion of the cytometer, the fluors are generally destroyed (through photobleaching), so that particle cannot be re-assayed without stripping off the (rather tightly bound) Ab labels and re-labeling. Fluorescence measurement of a natively fluorescent particle (i.e., molecules) may result directly in photo-destruction of the particle. Direct electrochemical detection also generally results in chemical alteration of the analyte.

For the particular case of detection of bacterial spores (of great interest for anti-biological warfare/counter-terrorism applications), classical microbiological methods, ELISAs, Ab-flow cytometry, and PCT have been applied, with their attendant advantages and limitations. Various methods have been developed that either do not require MRMs, or use other transduction mechanisms. Rosen, et al., Bacterial Spore Detection and Determination by Use of Terbium Dipicolinate Photo-Luminescence, Analytical Chemistry 89 (1997) 1082–1805, have reported that when endospores are incubated with terbium chloride, a photoluminescent complex is formed with spore case calcium dipicolinate. After filtration, a detection limit of $4.4\times10^5$ C.F.U./mL is obtained. Gatto-Menking, et al., Sensitive detection of biotoxoids and bacterial spores using an immunomagnetic electrochemiluminescence sensor, Biosensors and Bioelectronics 10 (1995) 501–507, have developed an immunomagnetic sensor for biotoxoids that uses a commercial electrochemiluminescence analyzer (ORIGEN®). A spore detection limit of 100 has been reported using this method.

Electrode arrays have been a topic of interest as miniature sensors for twenty years. In summary, these devices use microfabricated electrode arrays to detect a variety of environmental and biological compounds. These patents all use direct coulometric detection of the analyte by constructing on-chip electrical circuits to monitor individual currents directly as a function of time. A range of other electronic sensors, coupled with MRMs, have been proposed for pathogen detection wherein a change in the impedance signature of the sensors element occurs when particles bind to the MRM. These include, in particular, capacitance and impedance-based measurements on microelectrodes, and miniature oscillators of various kinds. Although the sensor element we describe does depend for its operation on the general concept of a change in the impedance of the element when the particle binds to the MRMs, it is fundamentally different, in that it operates on a single particle, statistical basis, and has a microscopic structure that makes this possible.

From the above summary it appears that the desirable properties for an improved sensor design are: 1) the ability to work at the statistical limit of sensitivity, 2) single-step operation, 3) continuous operation, 4) simplified reagents and fluidic systems, 5) ease of scaling to improve throughput, 6) low consumption of power and reagents, 7) non-destructive measurement of the particle.

The present invention provides considerable advantages of the prior known approaches to particle detection. The sensor element or device of the present invention has been demonstrated to respond to a single particle. The devices and methods of the invention do not require a prior or subsequent labeling step of the particle, though there are methods for use of the devices where such steps might be incorporated with some advantage. The detector devices of this invention represents a substantial improvement over electrode array detectors using traditional potentiostatic control/monitoring by simplifying the current measurement apparatus and allowing an increase in the information density of the detector. Their mode of operation allows single particle tracking and real-time monitoring of thousands to millions of active elements on a miniature device. It is not feasible to construct a million element electrode array and monitor current with a million potentiostats in a small device. The particle detector and method of the present invention employ a surface-attached specific affinity components to selectively capture a particle on elements of an array of single particle sensors. The particle detector array may contain a very large number of elements, or only single detector elements may be used. In addition, the invention includes a capacitive read-out circuit for electrochemical measurements which is more effective to the conventional potentiostatic control circuit previously used in electrochemical measurements.

SUMMARY OF THE INVENTION

It is an object of the present invention to provide a single particle electrochemical detector.

A further object of the invention is to provide microelectrode particle detectors.

A further object of the invention a device for single-particle detection and a method for using the device to achieve extremely high sensitivity detection of specific particles.

A further object of the invention is to provide an array of single particle detector devices to enable detection of a single specific type of particle, or for detection of a range of particle types.

Another object of the invention is to provide microelectrode detection devices with surface-attached, affinity ligands that bind selectively to some target particle species.

Another object of the invention is to provide single-particle detection devices where the electrodes electrolyze chemical species present in the particle-containing solution, and particle interaction with a sensor element modulates its electrolytic activity.

Another object of the invention is to provide devices for affinity-based electrochemical detection of particles with single-particle sensitivity, and where the devices may be employed as single sensors or may be configured in arrays.

Another object of the invention is to provide single or an array of detector devices which are connected to a capacitive read-out circuit.

Other objects and advantages of the present invention will become apparent from the following description and accompanying drawings. Basically the invention involves single-particle electrochemical sensor devices and methods for using these sensors to achieve extremely high sensitivity detection of specific particles, which may be cells, bacteria, viruses, aggregates, immunocomplexes, molecules, or ionic species. The devices and methods are based on microelectrodes with surface-attached, affinity ligands (e.g., antibodies, combinatorial peptides, glycolipids) that bind selectively to some target particle species. The microelectrodes have a specific geometry tailored for single-particle detection. The devices may be used individually, or as arrays, and are connected via a capacitive read-out circuit, and provide advantages over current affinity-based assays and sensors. The micro- or nanoelectrodes of the devices are situated in wells or surface depressions that have dimensions of the scale of the particle to be detected.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
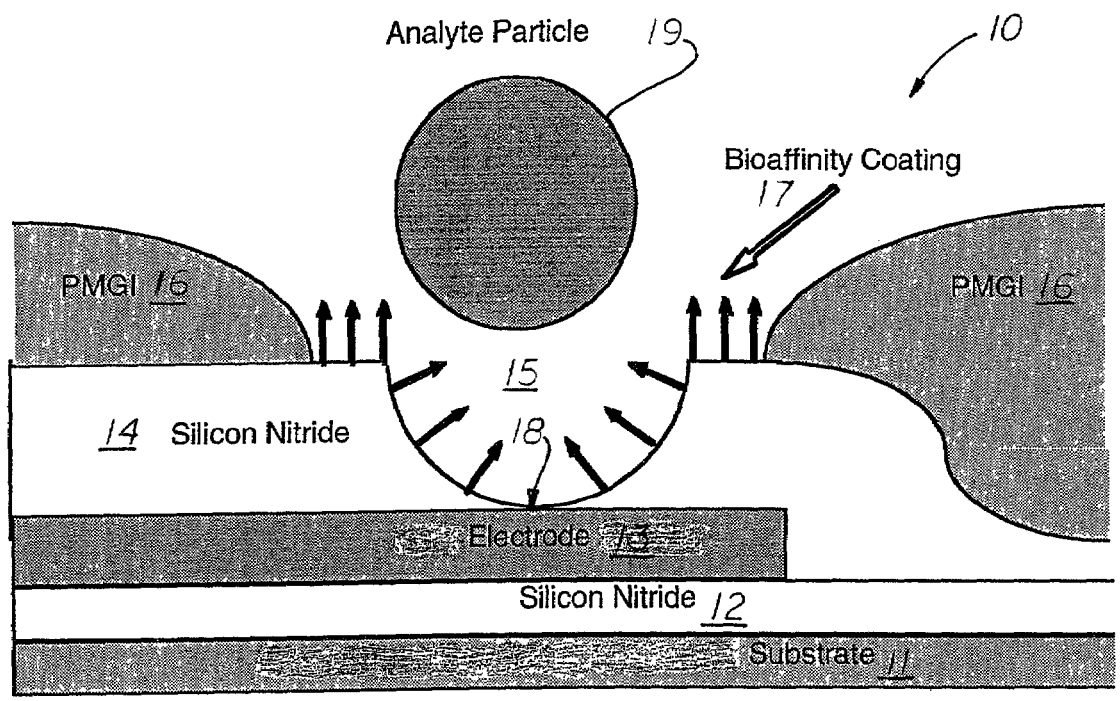
FIG. 1 is a schematic cross section of a single-particle detector device made in accordance with the invention, and showing the matched geometry of the device and a target analyte particle.

The present invention, described hereinafter, involves devices for affinity-based electrochemical detection of particles with single-particle sensitively. The particles can be cells, bacteria, viruses, aggregates, immunocomplexes or molecules. The devices described may be employed as sensors or assays for a single type of particle, or for a range of particle types, and may be configured in arrays having both these attributes. Also described are methods for using these devices to achieve extremely high sensitivity and high specificity detection of specific particles. These devices and methods would generally be used as sensors for particles dissolved or suspended in a solution.

These devices and methods employ a surface-attached specific affinity components (e.g., antibodies, combinational peptides, glycolipids) to selectively capture a particle on elements of an array of single particle sensors. Such as array might contain a very large number of elements, or consist of even a single element. The first device described is the individual sensor element (referred to below as an element), which is a micro- or nanoelectrode situated in a well or surface depression that has dimensions of the scale of the particle to be detected.

Capture of a single particle by the affinity material (referred to below as the ligand) associated with an individual element affects the electronic activity of that element in the following manner. Charge transfer currents may be generated and collected at the elements using a reversible redox couple recycled between its oxidation states by the element's microelectrode and a counter electrode. (The counter electrode need not be part of the element, but could also be incorporated into the element.) Single-particle capture by the element blocks the access of reducible or oxidizable material in solution to the surface of the microelectrode, disrupting the redox cycle at that electrode or, if that particle is able to donate or accept an electron, directly contributes a specific and finite number of charges, which will produce a transient response component, to the electrode current at this surface. The change in electrical activity subsists as long as the particle is held by the ligand in or on the element, except in the case of any redox activity on the part of the particle, which will be transient in nature. This change can be monitored using coulometry, impedance analysis or electrochemical charge storage and processing via capacitive read-out. The second device described is a novel circuit for accomplishing the capacitive readout of an element. On the other hand, it is possible in principal to directly monitor binding to the element without the use of an added redox couple by monitoring changes in the capacitance or impedance of the element.

The utility of these elements may be enhanced if they are employed as an array of individually monitored microelectrodes. For example, if one desires to measure the concentration a certain type of particle (referred to below as the target) in a solution, a surface covered with a number of identical elements, each with a ligand coating that binds to the target, may be used as a sensor for this target. Increasing the number of elements enhances the probability f capture of a particle by at least one element. Alternatively, different affinity ligands may be used in different regions of the array, or even for each element, allowing many different targets to be detected, or providing distinct affinity interactions for a single target, so that the target may be detected with high reliability. In such arrays, a single counter electrode may be common to all of the elements in the array, or some number of counter electrodes distributed amongst the elements.

The third device circuitry allows the array to be addressed in a row-column manner. As the number of elements grows in such in array, it becomes increasingly impracticable to run separate leads to and from each element in order to make non-interfering electrochemical measurements. Two different approaches for reading the electrochemical activity of the array are provided. Each circuit has some features in common with those used in certain solid-state imaging devices (charge coupled device chips or active pixel photodiode imaging arrays), However, they are completely distinct in other aspects, such as their incorporation of the novel capacitive readout circuit as part of their architecture, and the fact that they perform measurements of electrochemical, rather than photoelectric activity. In the first version of this circuit, microlithographic processing is used to fabricate, in the substrate beneath each element, the active solid-state devices necessary to read out that element. In the other version of this read-out circuit, the charge transfer current from the electrode is stored in a capacitor at each array element and can be quickly processed by sequentially moving and reading each charge storage bin. The method of charge processing is novel, but approximates the technique of charge manipulation used in Charge Coupled Device (CCD) cameras.

Also described below in detail are methods for employing these elements to measure the presence of particles. An ordered array of individually monitored elements opens up additional possibilities for the use of this new type of sensor. In particular, the response of such an array could be analyzed to allow spatio-temporal tracking of the capture/release of a particle. This would allow both transport characteristics (e.g., diffusion coefficient) and binding and release kinetics of the particle to be determined. In this way, chemically similar, but different size, or similarly sized but chemically dissimilar types of particles could be discriminated from one another. This constitutes a new method of single-particle discrimination for particles having chemically similar surface characteristics.

The single-particle electrochemical sensor element or device described hereinafter is intended to allow solutions or suspensions of particles in a liquid sample to be analyzed and individual particles of a given type to be detected if they are present in that sample. It is essentially a miniature electrochemical sensor that changes its electrical activity when a particle is bound to it. The sensor element will respond directly when a particle binds to it, without the need for additional washing, fixing, or addition of reagents after the particle binds, though the liquid in the sample may or may not contain added compounds than enhance the performance of the sensor element. The binding of a specific type of particle may be arranged by using affinity coatings on parts of the device. As described below, there exist affinity-based assays and sensors that measure changes in electrochemical signal when materials bind to the sensor/assay surface. The device described here is not simply a miniaturized version of these sensors, however.

The novel feature of the single-particle electrochemical sensor element described hereinafter is the relationship between the geometry of the electrode element and the size and shape of the target analyte particle. This relationship is shown schematically in FIG. 1. The element, referred to as a pixel below, consists of a microelectrode that is generally situated in a surface recess (referred to as a well) that fits the particle to be detected. (For disk-like or planar analytes the electrode might be flush to the surface.) The electrode may be a disk, an annulus, or possibly a more complex shape. There may also be an affinity coating that has been deposited on or around the electrode. The coating may be surrounding the electrode, on the sides of the well, located on islands of insulator on top of the electrode, or immobilized to the electrode itself. In addition, there must also be some means of forming an electrical connection to the electrode for purposes of measuring its electrical activity.

As shown in FIG. 1, the single-particle device or element, generally indicated at 10, comprises a single crystalline silicon mechanical substrate 11, a PE-CVD silicon nitride layer 12, a titanium/platinum (Ti/Pt) microelectrode 13, a layer 14 of PE-CVD silicon nitride having a depression or well 15 therein, a polydimethylglutarimide (PMGI) encapsulation layer 16, and a bioaffinity coating 17 that is deposited on the surfaces of well 15 except directly above the microelectrode 13, as indicated at 18. The well 15 is of a partial disk shape, which corresponds to the shape of an analyte particle 19 to be captured in the well 15.

By way of example, substrate 11 in addition to single crystalline silicon may be composed of silicon-on-sapphire, or silicon-on-insulator (SOI), and have a thickness of about 10 µm to about 2000 µm. Layer 12, in addition to silicon nitride, may be composed of any similar etchable semiconductor material, having a thickness of about 10 µm to about 2000 µm. Besides titanium/platinum alloy, microelectrode 13 may also comprise carbon or noble metals such as platinum, gold, rhodium, palladium or alloys of these metals and may have a thickness of a few microns to several hundred microns. Layer 14 comprises silicon nitride having a thickness about equal to a half the diameter of the particle of interest such that the bottom edge of well 15 is very near the surface of microelectrode 13. Layer 16 thickness varies in accordance with the location thereof. The bioaffinity coating 17 may have a thickness of a few nanometers to a few hundred nanometers and may be composed of antibodies, combinatorial peptides, glycolipids, or an amino acid.

The key attribute of the element is that binding of a single particle to the element results in a substantial change in the measured electrical activity of the elements. This feature is a result of the element's microelectrode matching the size of the particle. A single particle binding to the element can thus affect a substantial portion of the surface of the microelectrode of a given element. On the other hand, if a number of elements are present (i.e., in an array), a single particle will only effect one element at any given time. Monitoring of the individual electrical activity of one or more elements enables single particle detection when a significant change in the electrical activity of a single element is observed.

The present state of microlithography allows electrodes and wells on the order of one micron in size to be fabricated (see below). Elements with such features are on the appropriate size scale to allow detection of individual bacteria. As fabrication technology advances, it will be possible to reduce the size of the sensor by several orders of magnitude, allowing detection of ever smaller analytes such as viruses and large molecules such as DNA. It is also possible to use the element without affinity material, if the well has a particular shape that allows only particles of a certain size and shape access to the electrode surface.

Electrochemical affinity-based assays have been reported, (see Richert, et al., "A 'Mixed' Self-Assembled Monolayer for Impedimetric Immunosensors", Biosensors and Bioelectronics 11 (1996) 757–768; and Blonder, et al., "Development of Amperometric and Microgravimetric Immunosensors and Reversible Immunosensors Using Antigen and Photoismerizable Antigen Monolayer Electrodes", J. Am. Chem. Soc. 119 (1997) 10467–10478). However there are important differences between the device described here and those reported in the literature; namely, previous electrochemical sensors respond to the integrated signal from the entire electrode surface and thus include multiple binding events (many thousands or more of particles). The single particle electrochemical sensor responds to only single analytes of a defined geometry. The single particle electrochemical sensor also responds in a digital fashion (shown below) to a single particle binding event. This is advantageous and in contrast to previously reported sensors that respond in a continuous manner to analyte concentration.

Figure 2:
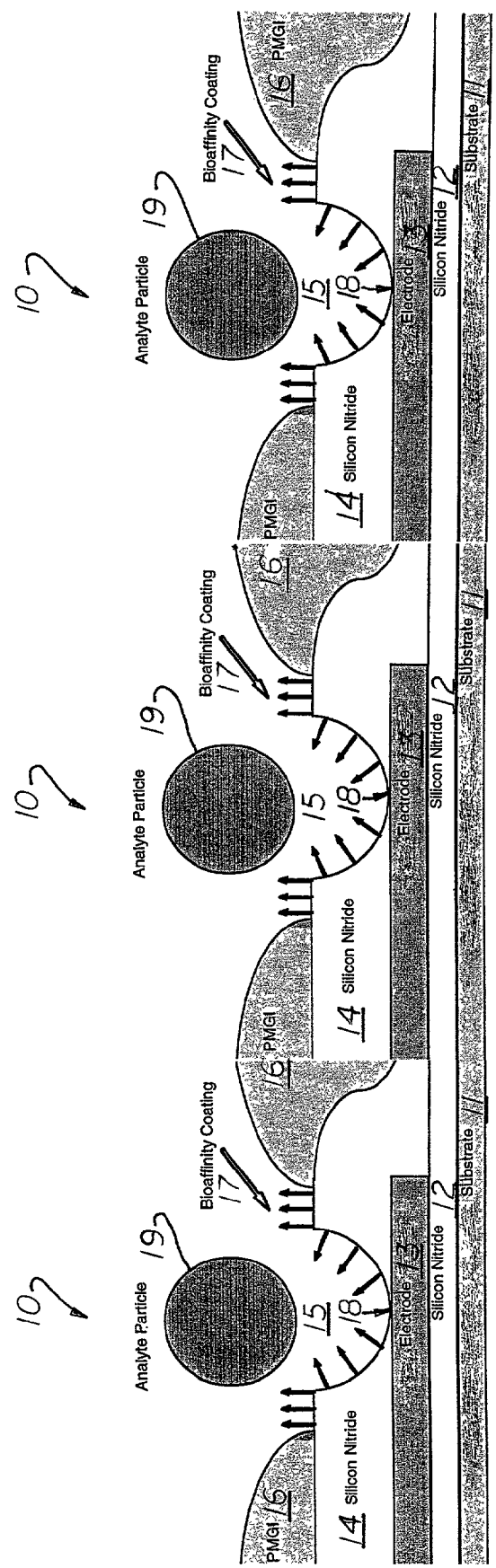
FIG. 2 illustrates an array of the devices of FIG. 1.

The electrode elements, illustrated in FIG. 1, can be fabricated and used singly or in arrays. FIG. 2 illustrates a three (3) element array utilizing the elements of FIG. 1. As shown in FIG. 2, the array comprises three (3) elements 10, each constructed as shown in FIG. 1 and provided with corresponding reference numerals.

Figure 3:
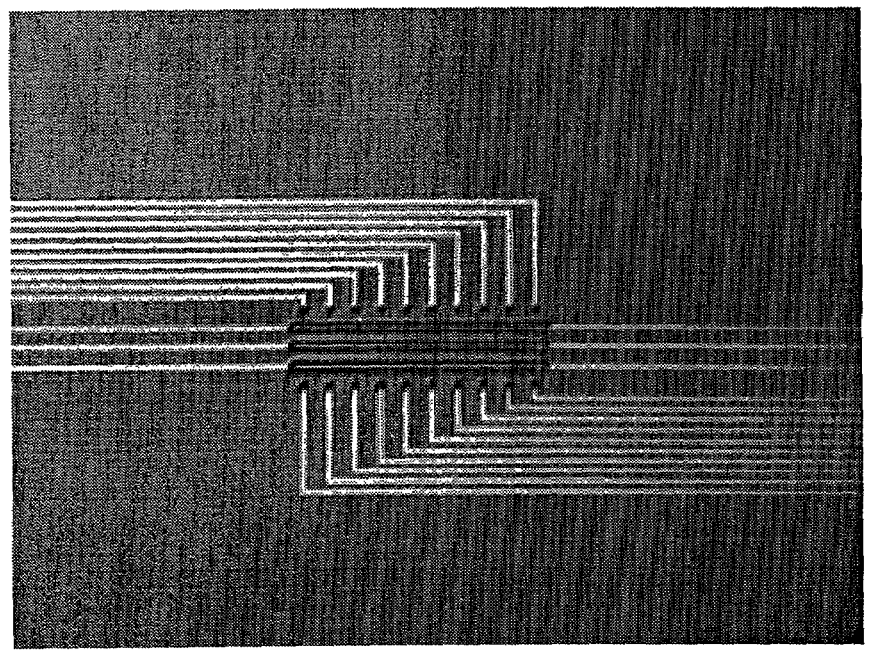
FIG. 3 schematically illustrates the single-particle device in a twenty (20) device array chip.

FIG. 3 also illustrates, on a modest scale, an array of detection devices or elements. It is certainly possible, although cumbersome, to make a large array with many wire-bonded connections. As shown in FIG. 3, a twenty (20) element array chip is provided with ten (10) elements on each side of an three (3) electrode assembly. Sections below address better ways of reading out the array that facilitate using large arrays to increase sample volumes and sensitivity. A variety of other electrode geometries could be described in addition to the configuration shown.

We have constructed a small array of prototype elements and demonstrated their function. Microelectrodes were constructed on a p-type silicon substrate using mircofabrication technology. The working electrode array elements is a recessed well-like structure approximately 1 µm deep and 1 µm in diameter as shown in FIG. 1. The shape of the element is tailored to matched the geometry of the target analyte particle. At the bottom of each element well, or pixel, was a photolithographically patterned platinum collector electrode. A veriety of electrode materials could be used, including carbon or gold. Trial systems have been made that consist of twenty (20) pixels and three (3) generator-reference platinum electrodes as shown in FIG. 3. The pixel well is constructed by isotropically etching silicon nitride and results in a sloping bucket-like surface near the platinum collector elctrode surface. The silicon nitride is then encasulated in polydimethylglutarimide (PMGI), leaving a region of silicon nitride exsposed along the top of the pixel as shown in FIG. 1.

Portions of the silicon nitride surface in or around each pixel can be chemically modified by the addition of selective affinity coatings. For example, using silicon alkoxides such as aminopropyltriethoxysilane (APTES), reactive amine groups may be covalently attached to the surface. The silanized nitride is then further adapted or "derivatized" with antibodies or other appropriate "biorecognition" coatings than enable the pixel to selectively bind an analyte of interest, or the pixel can be used as an intelligent filter to provide information on particle size without a bioaffinity coating.

Optimal function of the element depends on proper localization of the affinity ligands. Localization was accomplished in the example described here by controlling the size and shape of the area of silicon nitride left exposed. Nitride regions away from the well are covered with a polymer insulator, in this case PMGI. The silanization procedure described above can result in the exposed silicon nitride regions being "derivatized" (i.e., covered with amine groups) through its available silane groups, while the vast majority of the polymer surface is not. Materials deposited directly on the metal electrode surface may be removed electrolytically. It should be noted that the geometries of exposed nitride and electrode disk shown here is only demonstrative. Other arrangements may work better to accomplish the optimal capture and positioning of the particle so that it maximizes its exposure to the electrode or maximally blocks transport of solution species to and from the electrode (see first method.) An example of this would be the fabrication of a disk of nitride in the middle of the disk electrode. It is also possible to localize the deposition of the affinity material through patterned microlithography, or by using selective material "derivatization" other than silane/silicon nitride (e.g., gold/thiol if gold is patterned where ligand is desired).

Figure 4:
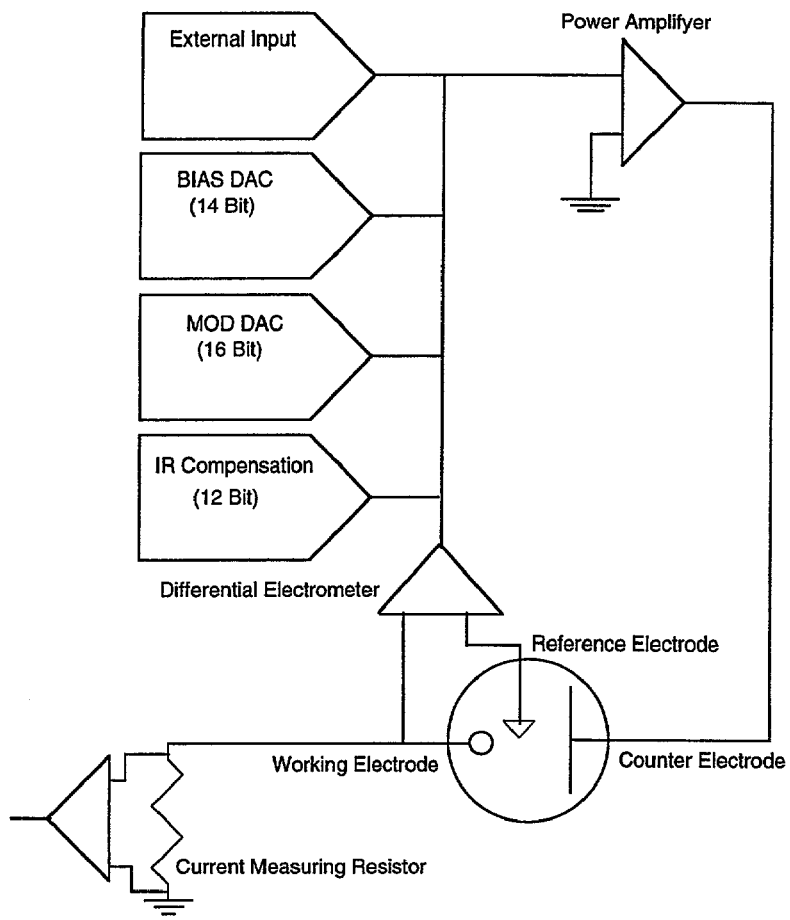
FIG. 4 is a schematic of a potentiostatic control circuit used in electrochemical measurements.
Figure 5:
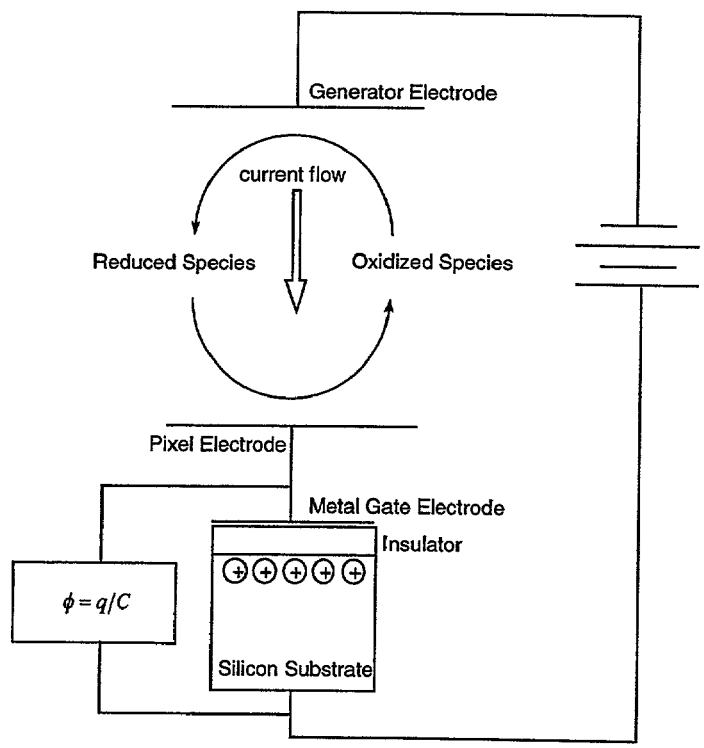
FIG. 5 is a schematic of a capacitive read-out circuit.

Electrochemical techniques are some of the most classical and sensitive analytical tools. The analyst typically performs a measurement of the current at a working electrode and relates the magnitude of the current to the concentration of a species in solution. The measurement is most often performed with a potentiostatic control circuit shown in FIG. 4. It is a disadvantage to use such a potentiostat to measure an array of thousands or a million electrochemical sensors because of the size and complexity of the instrument. This is true whether the sensors in question are the single-particle sensing elements proposed here, or a variety of other sensor types. FIG. 5 illustrates a novel capacitive read-out circuit that can be easily microfabricated into miniature highly integrated electronic devices similar to commercial charge-coupled-device optical cameras. This read-out is novel, interesting, and useful because it allows the measurement of electrochemical activity on a large number of electrodes without the use of complicated electronic components present in a potentiostat.

In using the sensor element 10 described above, particle binding information is contained in the magnitude of the current flowing between the generator electrode (counter electrode) and the collector pixel electrode (an ultra-microelectrode located near the bottom of the well). As an alternative to using a potentiostat to acquire this binding information, it is possible to use the electrochemical current to inject charge into a Metal Oxide Semiconductor (MOS) capacitor and measure binding by reading the voltage of the MOS capacitor in periodic intervals. A schematic of this circuit is shown in FIG. 5. The circuit consists of a generator electrode that is electronically coupled to a liquid or a solid polymer electrolyte by a charge-transfer reaction. Current is carried to the collector pixel electrode by ions in the electrolyte matrix and then into the pixel by another charge transfer reaction at the platinum surface. The charge of the capacitor is then measured and the voltage, $\Phi$, is indicative of the amount of charge passed.

The innovative nature of this capacitated read-out circuit lies in its unique method of charge injection used to acquire electrochemical information. Established commercial charge storage and read-out circuits are generally used for optical imaging or measurement applications, and all of them work using an optical or photo-transduction pathway. That is, charge is injected into the microfabricated structure by absorption of a photon by the semiconductor substrate this absorbed photon creates an electron-hole pair and, subsequently, the holes (or electrons) are collected and processed in an orderly fashion. This scheme is the basis of operation of many charge-coupled device architectures like miniature CCD cameras. If the electrons were generated by a heterogeneous electrochemical reaction, rather than electro-optically, stored electrons could leak back into solution depending on the bias of the metal electrode surface and the kinetics of the charge-transfer reaction. The device described in this report effectively decouples the charge-transfer and processing mechanism from the charge-injection step. The charge-processing and read-out mechanism involves a series of optically transparent polysilicon gate electrodes. These transfer-gate electrodes must not contact the electrodes, must not contact the electrolyte solution nor interfere with the electrochemical charge-injection step. The transfer-gate electrodes only serve to move trapped charge packets through the semiconductor substrate and ultimately to a device that can quantize the amount of charge present in these packets.

There are two events that form the basis of CCD operation. A charge must be injected into the read-out device; that charge must then be moved around and processed in an orderly manner to acquire information about the image. The post-injection charge transfer is accomplished by a complex network of polysilicon gates overlayed on the silicon substrate. A CCD camera collects photons over a period of time by allowing those photons to pass unhindered through the charge-transfer gates. The FIG. 5 read-out circuit does not use photons to inject charge but relies upon an electrochemical reaction at the surface of an electrode to charge up. This is the fundamental difference between the CCD camera and the capacitive read-out device described here. One cannot use a commercial CCD device to perform electrochemical imaging because the charge injection surface must be decoupled from the charge transfer gates. This decoupling requires an array of metal electrodes that penetrate the gate layer and deposit charge into the silicon substrate. Once that charge is deposited, then the transfer gates can process the integrated charge to form an image of the electrode array activity. These novel electrode-gate structures are described below.

In an array of sensors of the architecture proposed above is created and each is measured using a capacitive circuit of the type described above, then either of the following two devices could be used to read out this array. These devices provide for addressing the individual pixel elements of an electrochemical sensor that is comprised of an array of these elements, and for processing the electrochemical charge packets that are created in each element.

A. Charge-Coupled Device

Figure 6A:
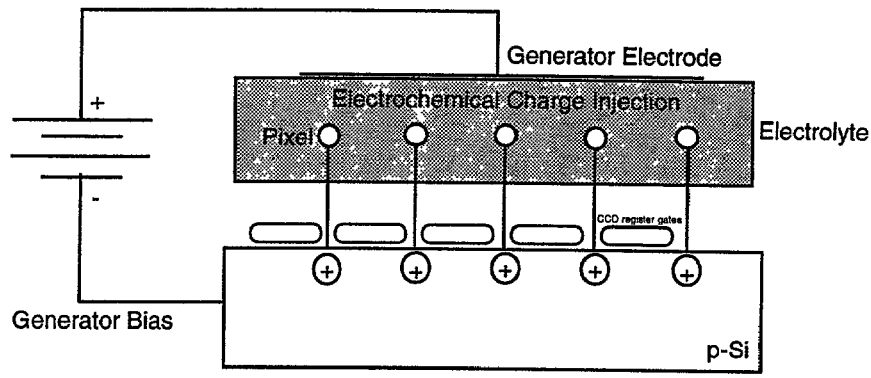
FIGS. 6A, 6B and 6C schematically illustrate a charge coupled device read-out.
Figure 6B:
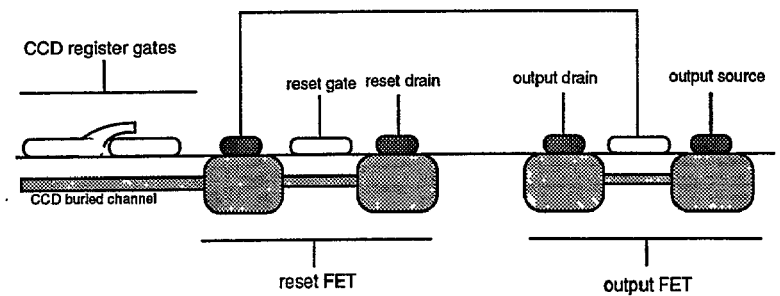
Figure 6C:
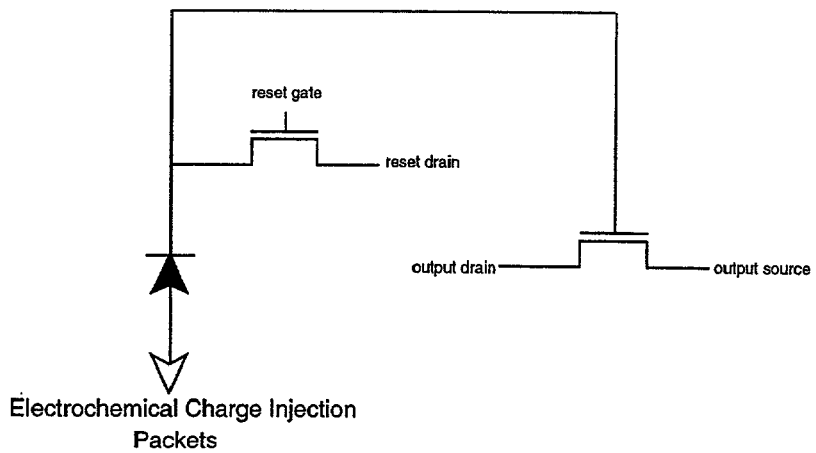

FIGS. 6A–6C show that a charge packet which has been injected electrochemically under one MOS (metal oxide semiconductor) gate electrode held at a fixed potential will spread along the silicon/insulator interface when a neighboring electrode is turned on to the same or higher (for negative charge carriers) potential than the generator bias. When the potential of the original storage electrode is reduced (for negative carriers), the charge packet is completely transferred into a new location. This process is referred to as charge coupling. A 3-phase system of clocked transfer electrodes is used to move charge packets in a bucket-brigade fashion. Charge-packet detection is realized by a pair of Field-Effect Transistors (FETs) located near the end of the buried channel along which charge coupling takes place. In our device, many electrodes tied together in a periodic manner can be used to individually address a matrix of pixel electrodes that have electrochemically injected charge packets.

B. Active Pixel Device

Figure 7A:
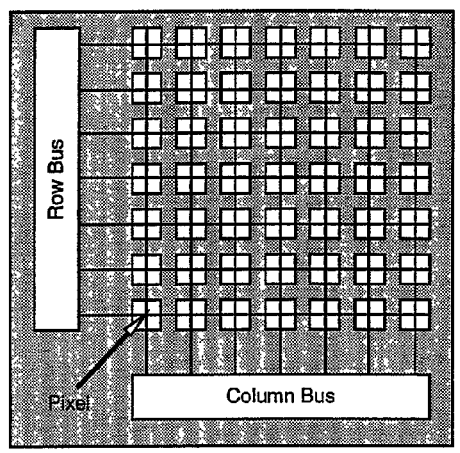
FIGS. 7A and 7B schematically illustrate a CMOS active element read-out.
Figure 7B:
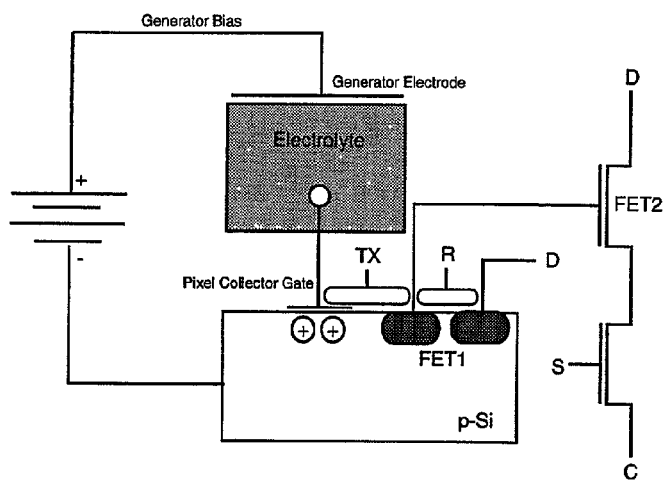

An alternative method for addressing the individual collector electrodes, or pixels is active pixel technology which incorporates an active charge detection circuit at each pixel element and is unique in the sense that this operation is done at each element and provides a means for random access to any pixel. The overall architecture for this device is shown in FIGS. 7A and 7B. The generator bias is set to inject charge into the pixel collector gate and after a suitable integration time, the charge packet is read by first biasing TX more negative than the collector gate. The charge packet will be transferred into a source region of FET1 and thus create a voltage that can be used to modulate the transconductance of FET2. Following signal integration, all pixels in the row to be read are read out simultaneously onto column lines by selecting S. After charge processing, FET1 is reset by R.

Methods have been developed for using the single-particle elements or devices to achieve extremely high sensitivity detection of specific particles. The following sets forth a description of the methods:

1. Method for Affinity Assays with Indirect Electrochemical Readout

This method relates generally to the measurement of particles present or suspended in a liquid medium by the detection of selected affinity interactions. Complementary binding based on non-covalent interactions between macromolecules forms the basis of several types of assays and sensors, most of which are immunorecognition determinations. For our purposes, the difference between an affinity-based assay and an affinity-based sensor is that the assay is a method for making a single measurement of the concentration or amount of a specific analyte. A sensor may then be regarded as a device capable of autonomously or nearly autonomously performing many assays in sequence. From this perspective we have described devices above that could be classified as sensors. (Sensors that employ biological molecules or components such as antibodies are referred to as biosensors.) Our aim here is to describe how a single assay might be performed using one of these devices.

The method described here could be used with a number of different kinds of ligands, including antigen-antibody, lectin-carbohydrate, complementary oligonucleotides or nucleic acids, to create selective interactions between surface immobilized compounds and their complementary target binding particles in solution. The detector platform is a single particle electrochemical sensor element that has bioaffinity species immobilized in a region near the pixel electrode surface. The size and geometry of the region may be optimized to enhance the binding of specifically-shaped particles to the well associated with that element.

In a typical affinity assay, such as a sandwich assay, a surface coated with affinity ligands is exposed to a solution containing analyte particles. A certain proportion of the particles bind selectively to ligands during a defined incubation period, and then the surface is washed to remove materials that are bound non-specifically. Next the surface is incubated with a labeled (typically fluorescent) secondary ligand that binds to the particles immobilized by the first ligand. A second round of incubation and washing takes place, and then the surface is "read" (e.g., by measuring its fluorescence). Reuse of the assay surface is possible only if the binding interactions can be disrupted, all particles, secondary ligands, and non-specifically bound materials removed, and this regeneration step does not damage the original ligands. A sensor system may be constructed by incorporating the assay into a device that can autonomously record the signal from the label, and carry out the various additions of reagents, incubations, and washing. It is obviously preferable for sensor applications, and really for all types of measurements, if assays can be developed that do not require secondary ligands, and better yet do not require repeated incubation and washing. The assay we describe immediately below has these attributes.

In our method, a sensor surface that has one or more of the elements present is exposed to a solution containing analyte particles. The activity of the elements is then recorded. Should a particle bind to an element, that event will register, and the timing and duration of the event will be recorded. Based on the number of particles bound, the known affinity of the elements for the particle, the volume of sample, the degree of mixing of the sample, the concentration of particles in the solution, the time of exposure, the concentration of particles in the solution, and the uncertainty in this concentration measurement may be determined. This determination may be made based on direct calculation, or a previously measured calibration curve.

The method described here requires that the device platform be incubated or exposed to the liquid medium, for example by immersing the surface in a reservoir of solution, or using other means of wetting the surface such as a microfluidic system or flow cell. It may be desirable to use this sensor either by placing the sensor in a microfluidic system or a flow cell into which sample is introduced by means of pumps. The use of a microfluidic network provides a means to perform bioaffinity assays in a flow-through fashion that circumvents the tedious operation of sample preparation and culture growth procedure used currently.

Figure 9:
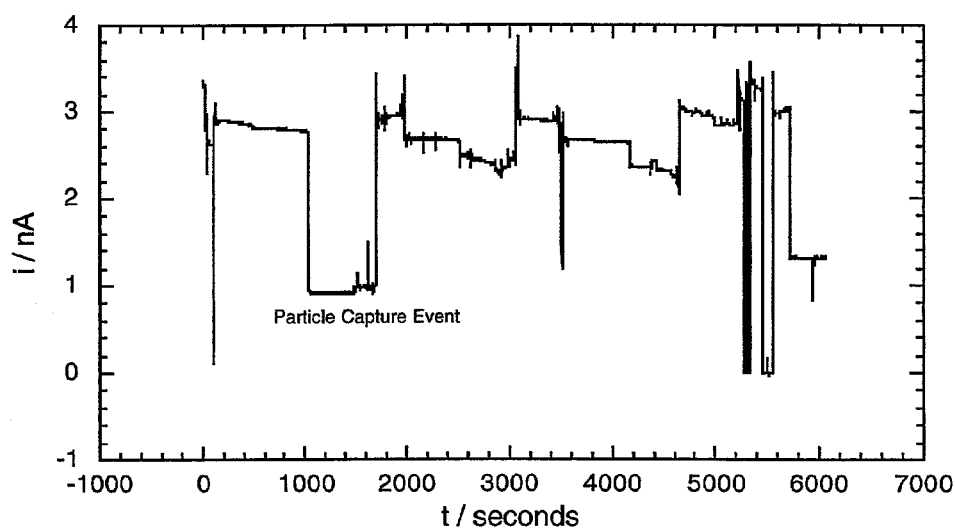
FIG. 9 illustrates digital current response to particle capture events.
Figure 8:
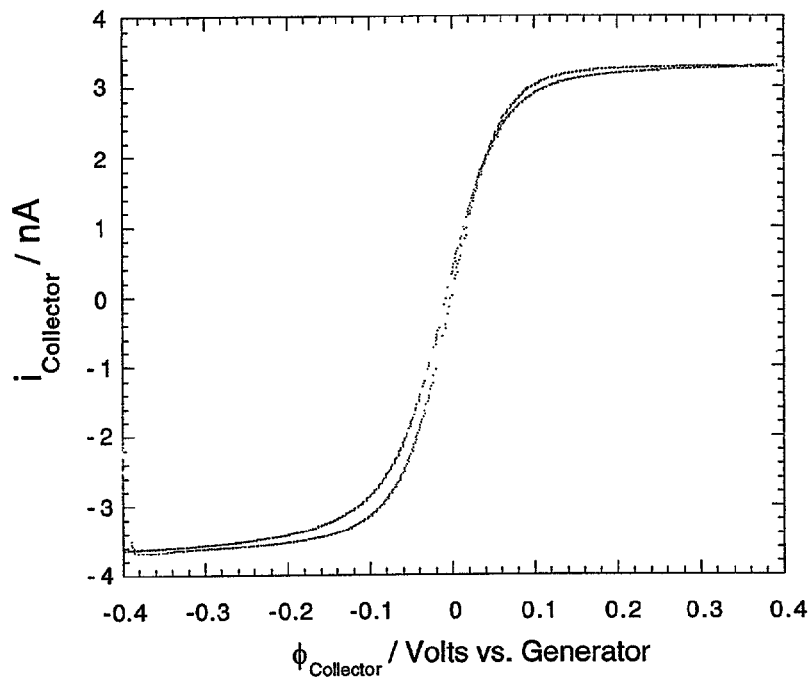
FIG. 8 graphically illustrates collector current as a function of generator bias voltage.
Figure 10:
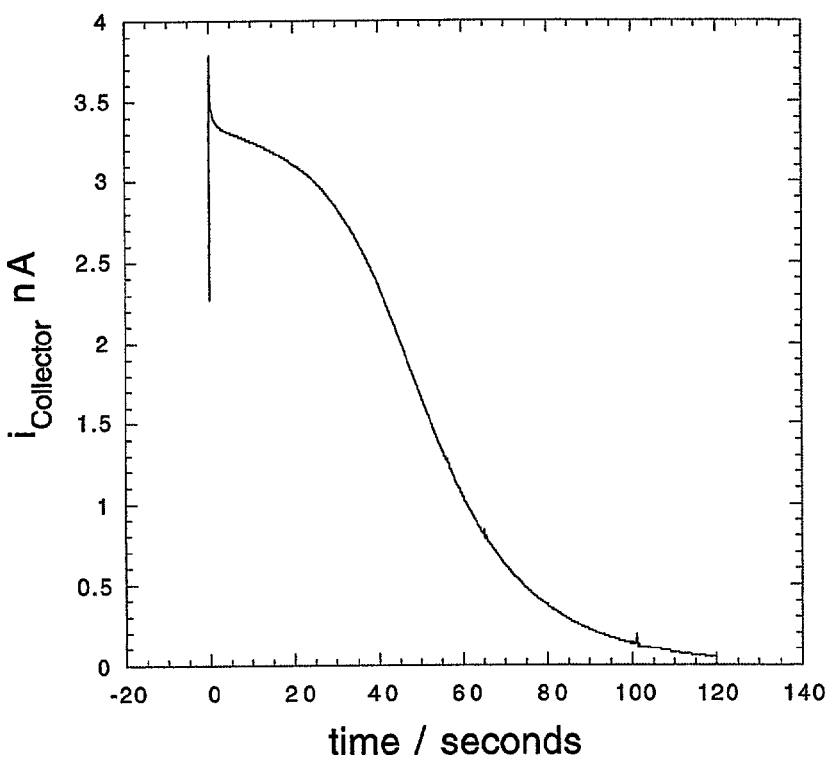
FIG. 10 graphically illustrates electrochemical charge storage.

This method can be realized using the single-particle electrochemical sensor device as an array chip that has been die bonded and packaged in a low-volume recycling liquid flow cell with a dissolved redox couple such as hexacyano-iron complexes. The nature of the dissolved redox species is not necessarily limited to these hexacyano-iron compounds, but can be any electroactive entity that has rapid and reversible reaction kinetics at the electrode surface. The iron complexes are reversibly oxidized and reduced at the collector electrode (pixel) and the generator electrodes when the generator is biased against the collector as shown in FIG. 8. The electrochemical current that flows from the generator electrode into the collector at the pixel is limited by the active surface area of the platinum electrode. The Platinum surface located at the bottom of the pixel is relatively small compared to the area of the Platinum generator and the current is typically ~3 nA as shown in FIG. 8 for an electrode area of 0.02 $cm^2$ and hexacyano-iron concentration of 20 mM. The collector current reaches diffusion-limited saturation at 200 mV applied potential. The device is operated by holding the collector electrode at 300 mV relative to the generator and monitoring the current level at the pixel. The device is then exposed to a solution containing an analyte particle. When a micron-sized particle is trapped in the pixel well, the collector electrode is no longer able to accept charge from the electrolyte solution. This causes an inhibition of the current and signals a particle-capture event. The current response to particle capture is essentially binary and shown in FIG. 9. This current can be stored in an integrated capacitor and read out at periodic intervals. The processing of this current response yields information regarding the binding kinetics of analyte particles. When a target particle is present in the flow stream passing over the detector surface, specific non-covalent affinity interactions will cause the particle to become trapped in the well area of the pixel electrode. This event is observed as a decrease in the integrated charge at that pixel.

2. Method for Creating Controlled Forces on Particles to Prevent Non-Specific Binding and Improve Particle Mixing The use of electrode arrays for particle detection depends strongly on the feasibility of separating extremely small polarizable particles in a complex background matrix of non-hazardous particles. This separation or fractional step is an integral part of the sensor platform. Dielectrophoretic (DEP) separation of particles can be achieved with microelectrode arrays described in the device section and programmed alternating current excitation waveforms applied to the generator electrode. Electrophoresis is the movement of particles with a net intrinsic charge in the presence of a DC electric field. DEP motion is determined by the magnitude and polarity of the induced dipole moment of the particle. This dipolar polarization is induced in a particle by the applied electric field and is strongly frequency dependent. The magnitude of the induced charge is small, equivalent to about 0.1% of the net surface charge normally carried by cells and microorganisms and can be generated in approximately one millisecond after excitation. If the polarizability of the particle is sufficiently different from that of the surrounding matrix, the particle will move in an inhomogeneous electric field. The interesting feature of DEP is that polarizabilities can result in positive or negative dielectrophoresis that is frequency dependent. Therefore, cells and microorganisms can have readily distinguishable DEP fingerprints as well as defined migratory behavior.

The electrophoretic or dielectrophoretic (DEP) effects induced by the electrode array device can be used to apply a force to particles near the collector electrode pixels. This force can be adjusted to exceed the binding energy of nonspecific binding of the particles and therefore enhance the detection of target species. Thus, we describe a method for increasing particle mixing in the sensor by DEP, and exploiting the array structure to facilitate the application of fields. The method involves performance of the assay as described above with dielectrophoretic sample imaging.

3. Method for Spatio-Temporal Tracking of Particles

The use of large arrays of single-particle sensor elements facilitates robust particle detection by allowing spatial and temporal tracking of binding events. Target analyte particles will bind to specific affinity coatings in the element well and will have binding kinetics different from background sample matrix entities. The transport of particles between wells will depend on transport coefficients such as the diffusion constant or electrophoretic or dielectrophoretic mobility that reflect properties such as size and charge and polarizability of the particle.

In the case of a measurement array that is incorporated in a fluidic cell with an imposed bulk liquid flow that is rapid compared to diffusion and dielectrophoretic mobilities, transport can be dominated by the bulk fluid flow, so than only the binding constant for a given particle with the sensor elements plays a differentiating role in its time of transport across the sensor array (this is analogous to the situation in various chromatographs, where the flow rate of a mobile phase controls velocity of free molecules and the strength of their interactions with column materials therefore control retention time). In this case, an example scenario is as follows: a particle binds to a particular pixel, changing it to the "off" (blocked) state. Some time later (time controlled by strength of binding), the particle leaves the pixel and is immediately carried by bulk flow across the array. If a collision with a subsequent pixel results in binding, it can be determined that the same particle is involved simply by knowledge of the bulk flow rate and the time at which the particle left its initial site. Again, its binding energy controls the time of binding at the new site. This process may be repeated several times as the particle makes its way across the entire array. The average of the binding times at each of the several sites on which it has stopped will be the best measure of the energy of interaction between the particle and the binding sites, and should lead to unique identification of this particle in many cases. Note that the correlation of multiple successive binding events for a single particle is exceptionally straightforward in this scenario, because the bulk liquid flow rate determines with some precision the expected time interval between release from one pixel and binding at another pixel that is a well-defined distance "downstream." Mass conservation may also be included as a constraint in this and other examples.

As a further example, consider the presence of a single particle in a fluid volume above the array, where there is no imposed bulk liquid flow. All pixels in the array are monitored at regular time intervals. The particle is confined in this value and diffuses about until it is captured, at which point an array element registers its presence as diminished current or less integrated charge on the associated capacitive element: the pixel "turns off." The particle is then retained for some period of time characteristic of its binding energy with the well's surface before it breaks off, diffuses away, is recaptured, etc. If the time interval between consecutive measurements of the array elements' current/charge state are sufficiently short, and the binding times for the particle sufficiently long, then the binding and release of a single particle will be registered by a specific pixel turning off and then, some measured time later, turning back on. Once released, if the same particle moves to and binds in a different location, it will create a similar off/on signature at that pixel. The probability that this pair of spatio-temporally separated off/on events is correlated, i.e., that they resulted from the very same particle, is a function of the time interval, the distance between the two affected pixels, and the particle's overall mobility (diffusion coefficient, electrophoretic mobility, and/or dielectrophoretic mobility), depending upon imposed fields. For instance, if one pixel turns off at the same instant that a pixel on the other side of the array turns on, it is very unlikely that the two events resulted from a single particle; the observed phenomenon must be due to more than one particle being present.

While a pixel could "spontaneously" turn off and back on in the absence of a specifically detected particle—as the result of electrical noise or the nonspecific binding of a different particle type—the time duration of such events will generally be quite different from the off/on time signature of a specifically detected particle, but lo the device can be constructed such that the probability of this is insignificant, or at least well characterized. More rigorously, the probability of this is insignificant, or at least well characterized. More rigorously, the probability that the observed phenomenon could be accounted for by a single particle with a given transport coefficient (e.g., diffusion coefficient) can be calculated (and this calculation could be modified by including the probability of spontaneous pixel activation), As binding and unbinding events (a pixel going on and off) accumulate, the average number of time intervals for which the particle remains bound, as well as the variance of this number, can be used to calculate the kinetic on and off rates for the particle binding, which can be compared to independently measured on and off rates for association of the particle with the affinity material. In this way, it can be determined if the particle is binding through Non-Specific Binding (NSB) or selective interactions. In general, then, the kinetic transport coefficients and affinities of a single particle may be measured by such an array.

The analysis described above applies quite generally to any array of elements capable of single particle detection. Another example of such a device would be an ultra-sensitive CCD camera used to image the position of a single fluorescent molecule or particle as it diffuses or is transported along a surface in a thin layer of liquid. Although the motion of the particle is observable at every position (as opposed to only when bound to a well), the positional information is recorded on a spatially discrete device (the CCD array) that is periodically read, so the spatio-temporal information is essentially the same type as would be recorded by an array of our elements. Aside from the differences in the complexity of the systems (the optical experiment requires fluorescent labeling of the analyte, a light source [generally a laser], high quality interference filters and optical design to eliminate excitation light), the physical information recorded is different in the optical system, in that it does not record whether the particle is bound to the surface, only where it is, and our device array will only record where the particle is when it is bound. If sampling is rapid compared to the binding and unbinding, the particle would appear stationary in the optical system when it is bound, so binding could be inferred from position and time. (It should be noted that the two approaches could be combined into a single device to give more complete information about the state of the particle.) The principle difference is that in the optical system, the labeled particle will generally photo-bleach after a brief interval. It is therefore difficult to use mass (particle number) as a constraint in analyzing the results from the array.

Another implementation of single particle sensors could be in the form of an array of immobilized living cells with receptors for a particle. Cells can be produced that have the property that they change their behavior in a recordable way when a single particle binds to their receptors. This might take the form of a change in the membrane potential of the cell (e.g., monitored by an array of electrodes), or the cells might emit light or become fluorescent (e.g., monitored by a CCD). In any case, the cells are turning the energy of a single binding event into the creation, destruction or transport of a number of molecules, just as our method turns a binding event into blocking the reaction of a large number or redox couples with the element's electrode. The cells might be expected to have a significantly higher background level of spontaneous activation, as their signal transduction is generally related to leakage of ions through membranes. As the array is scaled up in size, the "noise" from the spontaneous pixel activation may grow until it drowns out the binding information. For a large enough array this will certainly happen.

The method we now describe for utilizing arrays of single particle sensors for detection of small numbers of particles in large volumes could be employed with any of these devices. It is designed to work particularly well for such measurements when using the types of electrochemical arrays described above, because of their low spontaneous activation/deactivation, and the fact that their interactions with the particle are non-destructive, and require no pre-labeling. It is specifically designed to overcome the problem that arrays of single particle sensors can not simply be scaled in size in order to increase the sample throughput (in order to increase the concentration sensitivity by allowing a particle to be found in a larger volume) because spontaneous activation will eventually become more likely than particle binding.

The method assumes that the number of elements exceeds the number of particles. It can be implemented if the following conditions are given:

1. Two planar arrays of single-particle sensors, each of area A. The arrays are separated by a small gap of height h into which fluid of volume (A)×(h) may be introduced, and could be flat or curved (e.g., nested cylinders)

2. Measured values for the kinetic on and off binding rates of the target particle to the receptor, and the appropriate transport coefficient for this particle (e.g., 2D effective diffusion coefficient. If active but non-directional (i.e., DEP) mixing is used this would be a pseudo-diffusion coefficient, if a direction transport field is imposed, it would be a mobility).

With these given, the methods consist of:

1. Introducing a volume (A)×(h) of sample containing a redox couple and the particles to be detected into the sensor.

2. Recording the activity of the array at a time interval known to be short relative to the probability of a particle binding and unbinding or moving between wells when unbound.

3. Converting the activity of each element at each time point into a one or zero, depending on whether the level of activity indicates a particle was bound or not.

4. Calculating, based on the known probability per unit of time of the particles binding, unbinding, and being transported a given distance in that time, and using the constraint of particle number conservation, the joint probabilities that a particle bound at one time and place could be the same as another bound at another time and place.

5. Determining the number of particles present by determining which integral number N of particles best accounts for the joint probabilities observed.

Other methods for using the single-particle detector devices, either alone or in an array, include:

1. Methods for determining if the particles are not of the target.

2. Method for removing non-specific binding effects.

3. Modified method if finite particle lifetime or source or sink is involved.

It has thus been shown that the single-particle detection devices of this invention, when utilized alone or in arrays achieve extremely highly sensitivity detection of specific particles. The invention involves a capacitive read-out circuit which enables the use of a high number of devices in an array. Also, methods have been developed using the single-particle devices for affinity assays with indirect electrochemical readout, for creating controlled forces on particles to prevent non-specific binding and improve particle mixing, for spatio-temporal tracking of particles. The sensors utilizing the single-particle detection devices provide a substantial improvement over electrode array detectors using traditional potentiostatic control/monitoring by simplifying the current measurement apparatus and allowing an increase in the information density of the detector.

While particular embodiments of the detection devices, circuits, and methods for using the devices, along with materials and parameters, have been set forth to exemplify and teach the principles of the invention, such are not intended to be limiting. Modifications and changes may become apparent to those skilled in the art, and it is intended that the invention be limited only by the scope of the appended claims.

What is claimed is:

1. A device for affinity-base electrochemical detection of particles with single-particle sensitivity, comprising:
    an electrode:
    a first layer of insulation material disposed over said electrode, said first layer of insulation material comprising a thickness and a well extending into said thickness and located proximal said electrode, said well comprising an interior surface, wherein a portion of said interior surface is in contact with said electrode;
    an encapsulation layer disposed on said first layer of insulation material except in an area within the well and an area adjacent to a perimeter surrounding said well; and
    a specific affinity component attached to said interior surface except on said portion of said interior surface in contact with said electrode.

2. The device of claim 1, additionally including a substrate and a second layer of insulating material on said substrate, wherein said electrode is disposed on said second layer of insulating material.

3. The device of claim 2, wherein said surface-attached specific affinity components comprises a bioaffinity coating.

4. The device of claim 3, wherein said bio-affinity coating comprise an affinity ligand.

5. The device of claim 4, wherein said affinity ligand is selected from the group consisting of antibodies, combinatorial peptides, glycolipids, and amino acids.

6. The device of claim 2, wherein said first and second layers of insulating material comprise of silicon nitride.

7. The device of claim 2, wherein said substrate comprises single crystalline silicon.

8. The device of claim 2, wherein, said electrode comprises Ti/Pt.

9. The device of claim 2, wherein said encapsulation layer comprises of polydimethylglutarimide (PMGI).

* * * * *